United States Patent [19]

Mylrea

[11] 4,256,103
[45] Mar. 17, 1981

[54] AUTOMATIC SEQUENTIAL FLUID FLOW APPARATUS

[75] Inventor: Kenneth C. Mylrea, Tucson, Ariz.

[73] Assignee: James Paxinos, Tucson, Ariz.; a part interest

[21] Appl. No.: 950,329

[22] Filed: Oct. 11, 1978

[51] Int. Cl.³ ............................................... A61M 5/14
[52] U.S. Cl. ................................. 128/214 R; 128/227; 128/214 C; 222/145; 137/434; 137/113
[58] Field of Search ........... 128/214 R, 214 C, 214 Z, 128/227; 222/145; 137/434, 113

[56] References Cited

U.S. PATENT DOCUMENTS

| | | | |
|---|---|---|---|
| 2,090,273 | 8/1937 | Wagner | 128/214 C X |
| 2,549,409 | 4/1951 | Atkinson | 137/113 |
| 2,890,711 | 6/1959 | Parker | 137/434 |
| 3,177,870 | 4/1965 | Salem et al. | 128/214.2 |
| 3,667,464 | 6/1972 | Alligood | 128/214 C |
| 3,951,145 | 4/1976 | Smith | 128/214 C |
| 3,982,534 | 9/1976 | Buckman | 222/145 X |

FOREIGN PATENT DOCUMENTS

| | | | |
|---|---|---|---|
| 1138647 | 1/1957 | France | 128/214 C |
| 2282278 | 3/1976 | France | 128/214 C |

*Primary Examiner*—Dalton L. Truluck
*Attorney, Agent, or Firm*—J. Michael McClanahan

[57] ABSTRACT

Sequential, continuous delivery of separate intravenous fluid mixtures is facilitated by a float operated valve which automatically re-starts flow from a primary solution when the selected volume of secondary fluid has been infused. The float is contained in a calibrated volumetric chamber with a drug injection port, and valved connections to primary and secondary solutions. Selected volumes of primary or secondary solution can be added to the chamber and mixed with drugs inserted through the injection port.

Fluid in the calibrated chamber raises a float which closes a valve and stops fluid flow from the primary solution source. Fluid from within the chamber flows to the patient until very little fluid remains in the chamber and the float moves downward causing the valve to the primary solution to open allowing a continuous flow of intravenous fluid to the patient.

5 Claims, 2 Drawing Figures

AUTOMATIC SEQUENTIAL FLUID FLOW APPARATUS

BACKGROUND OF THE INVENTION

The present state of the art relative to infusing intravenous intermittent medications involves two methods, both of which share equally in the proportion of use in today's hospital practice.

The first method utilizes an in-line burette where a special intravenous (IV) set with a calibrated chamber in the IV fluid pathway in used for receiving a premeasured dose of a drug. The drug is injected into the calibrated chamber by means of a rubber sealed opening. Generally the primary IV solution is used to dilute the drug to a volume of 50 ml to 100 ml. The primary IV solution is then manually shutoff by a stopcock placed in the fluid pathway between the primary solution container and the calibrated chamber. The drug, diluted or not, enters the patient's body until the calibrated chamber is depleted at which time, the nurse must manually restart the primary IV solution. Failure of the nurse to restart the primary IV solution within a short period after the contents of the calibrated chamber are evacuated greatly enhances the opportunity for clotting within the patient's blood vessel about the tip of the intravenous cathetes.

The second method, the so called piggyback system, utilizes the drug in a small volume "mini-container" placed at a higher level than the primary solution container. Here tubing from the mini-container joins with the tubing from the primary solution container between the primary solution container and the patient. The tubing between the primary solution container and the junction with the tubing from the mini-container incorporates a check valve which permits flow of the primary solution only when it has the higher pressure head. Thus, fluid from the mini-container will take precedence. The primary solution resumes automatically after the depletion of the fluid in the mini-container.

Disadvantages of the piggyback system is that a new mini-container must be obtained for each administration of the drug, that no opportunity is permitted for primary solution dilution, and that the total amount of the drug is not administered as there remains in the tubing that amount of the drug which is below the level in the primary solution container. In addition, the piggyback system is inheritantly an expensive system.

Thus, it is apparent that there is a need for a device for intermittently infusing drugs into a patient's body, with or without primary solution dilution, in an IV arrangement or with a secondary solution with a sequential continuous intravenous flow.

SUMMARY OF THE INVENTION

Automatic sequential fluid flow apparatus and method for intravenous (IF) fluid delivery is disclosed where in the normal IV apparatus consisting of innerconnected primary solution container, calibrated volumetric chamber, and drip chamber, the calibrated volumetric chamber is modified by providing a float operated valve interiorly. When a secondary solution, nominally a drug, is to be administered intravenously, either in a diluted form with the primary solution or without dilution, the secondary solution is admitted to the calibrated chamber. Admission of the secondary solution is accomplished by injection through a rubber closed opening in the calibrated chamber, or by means of additional tubing connecting the calibrated chamber with the secondary solution container. In addition, it would be possible to dilute a drug injected through the rubber closed opening with the solution from the secondary solution container.

The presence of additional fluid in the calibrated volumetric chamber actuates the float operated valve which automatically terminates the primary solutions's entry into the calibrated chamber. The float operated valve continues to interrupt the primary solution until the secondary solution has exited the calibrated chamber at which time the float actuated valve automatically restarts the primary solution.

As a consequence there is a minimum of mixing of the two fluids at their interface for straight secondary solution infusion, or by means of second valve-controlled entry of the primary solution into the calibrated volumetric chamber, accurate dilution of the secondary solution with the primary solution may be facilitated.

Accordingly, it is an object of the subject invention to provide apparatus and method for interrupting a primary solution flow in an intravenous fluid delivery system for infusion of a secondary solution by utilizing the presence of the secondary solution in the intravenous fluid system.

It is another object of the subject invention to provide a means and method by which in a sequentially operated, separate fluid intravenous delivery system, the presence of a secondary solution stops the primary solution, infuses the secondary solution, and upon termination of the secondary solution, automatically restarts the primary solution.

It is a further object of subject invention to provide means of selecting volumes of one or more fluids which may contain drugs or into which drugs can be conveniently diluted for sequential intravenous infusion to patients.

DETAILED DESCRIPTION OF THE PREFERRED EMBODIMENT

Figure 1:
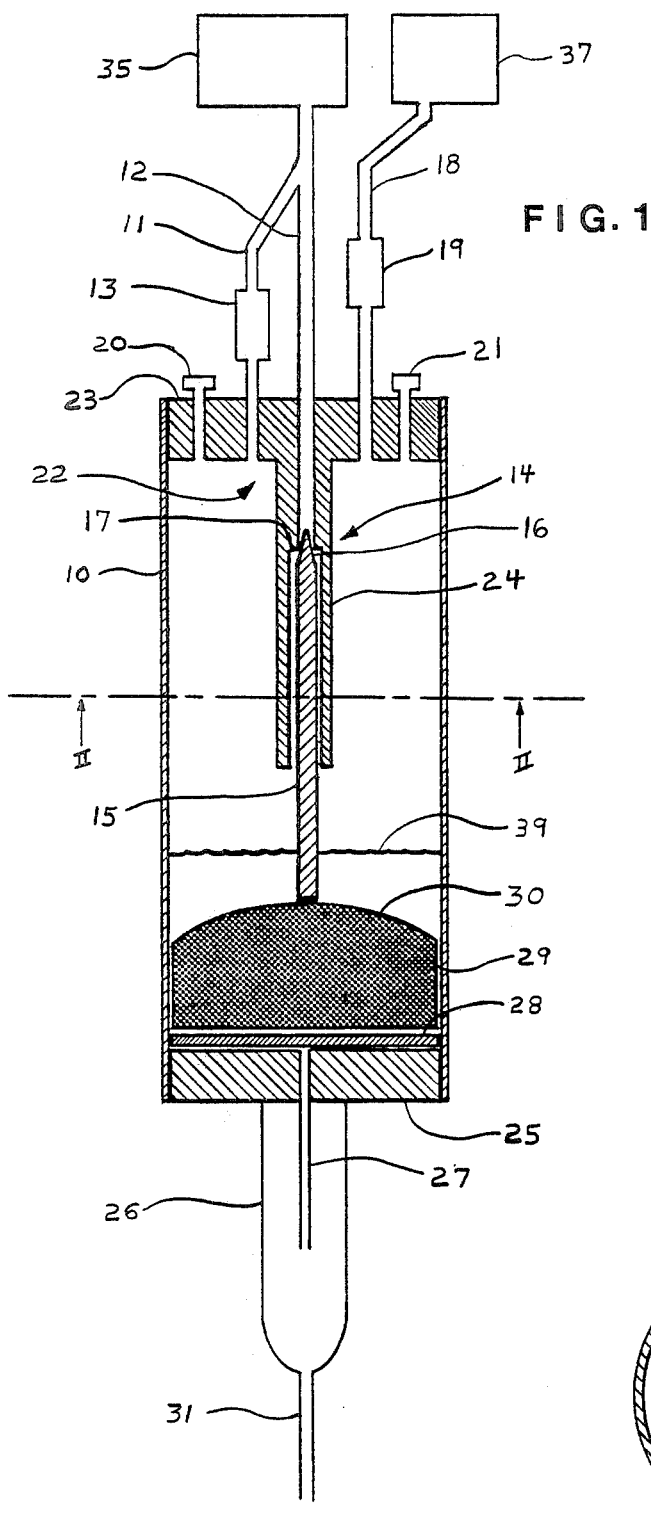
FIG. 1 is a cross-sectional view of the automatic sequential fluid flow apparatus.

Referring now to FIG. 1, a cross-sectional view of the subject invention taken along the vertical axis of the calibrated volumetric chamber is shown in detail. The calibrated chamber 10, which is in line with the intravenous solution containers to the patient receiving the solutions, receives the primary solution from the primary solution container 35 by one of the two inlets. In a straight flow arrangement, tubing 12 connects the primary solution container 35 to the top end 23 portion of calibrated chamber 10. Tubing 12 joins to the passageway through needle valve assembly 14 connected with top part 22 where flow of the primary solution is controlled by the float valve assembly later discussed. Additionally, through an inverted Y connection, tubing 11 connects with tubing 12 to direct the primary solution to flow valve 13 which in turn is in communication with the interior of calibrated chamber 10 through top end 23. On either side of top end 23 is non-wetable membrane bacteria filter 20 which passes air into the calibrated chamber to allow free flow of solution, and rubber sealed injection port 21 which permits direct injection of solution. Additionally penetrating top end 23 is the tubing 18 which in turn connects with the secondary solution container 37. Situated between secondary solution container 37 and top end 23 is flow valve 19.

The intravenous administration set which has been modified for the subject invention comprises all elements shown in FIG. 1 with the exception of the float valve assembly which will be further discussed; the needle valve assembly 14; the secondary solution container, interconnecting tubing, and flow valve; as well as interconnecting tubing 11 and flow valve 13. As is obvious, top end 23 in the original intravenous administration set must be modified to permit entrance of the secondary solution through tubing 18 and the bypass for the primary solution through tubing 11, as well as the joinder of needle valve assembly 14 to top end 23. It is anticipated that in the manufacture of the invention, a new top part 22 will be assembled with the stated modifications.

Needle valve assembly 14, which comprises two different sized partial passageways in an inward elongated extension of top part 22 permits the end 16 (normally pointed) of fluted shaft 15 to regulate the flow of primary solution into the calibrated chamber. Fluted shaft 15, which resides interiorly to valve guide 24 of the elongated extension portion of top part 22 surrounds fluted shaft 15 in a slidable manner, allows sufficient clearance for fluted shaft 15 to move freely longitudinally without binding on the sides.

Proceeding on down on the calibrated chamber 10 shown in FIG. 1, float 29 resides at the bottom, sitting on top of the membrane valve assembly 28 which permits the passage therethrough of fluid but not air. Float 29, which is sized to allow easy vertical sliding in calibrated chamber 10, is constructed of plastic in the preferred embodiment and has a hollow interior. Rounded top 30 of float 29 is so rounded to permit the primary solution, which escapes through needle valve 14, to run to the sides of and around float 29. It is noted that since it is desirable that a minimum of primary solution should be contained within the calibrated chamber 10, and that float 29 must regulate the flow of the primary solution by its floating position, the clearance on the sides between float 29 and the interior of calibrated chamber 10 is held to a minimum, subject to the above constraints. In addition, the length of the fluted shaft 15 in relationship to the position of the needle valve assembly 14 is so regulated that very small movements of float 29, pushing upon fluted shaft 15, will close the needle valve. It is anticipated that float 29 rising 1/32 to 1/16 of an inch should be sufficient travel to shut off flow. As it is obvious, the necessary rise in float 29 from turnoff to fluid flow is a function of all the factors which go to make up the calibrated chamber 10 plus the float valve. For example, for fixed distances between the two ends and standardized sizes of the top part 22 with needle valve assembly extention, changing the length of fluted shaft 15 directly affects the amount of fluid which will be beneath float 29 and in the calibrated chamber 10.

It is noted, as part of the invention, that fluted shaft 15 and float 29 are two separate elements, engaged only in a touching arrangement where the bottom end of fluted shaft 15 engages the rounded top 30 of float 29. While the float 29 and the fluted shaft 15 could be manufactured as one piece, manufacturing tolerances suddenly become very critical for the freedom of movement that must be inherent in float 29. This problem was solved by separating the fluted shaft 15 and float 29.

Directly below float 29 is the membrane air valve 28 as already discussed, followed in turn by base 25 which fits into calibrated chamber 10 in a watertight fashion. Centrally penetrating base 25 is drip tube 27 which permits the fluid interior to calibrated chamber 10 to drip into drip chamber 26, then passing by means of tubing 31 to the infusion cathetes in the patient (not shown).

The infusion rate of fluid into the patient is monitored by counting the drips per minute which fall from drip tube 27 into drip chamber 26.

In operation, and when it is desired that a secondary solution, such as a drug, be passed from secondary solution container 37 into a patient, flow valve 19 is opened permitting the secondary solution to flow directly into the calibrated chamber 10. Now if, as is customary, the same drug is administered in a measured amount on a regular time basis, secondary solution container 37 may contain sufficient volume for several administrations and a fixed amount of the solution can be allowed to accumulate in calibrated chamber 10 and thusly be infused into the patient. The amount to enter is controlled by flow valve 19.

After the secondary solution floods into calibrated chamber 10, the first effect is to raise float 29 the distance necessary to shutoff all flow of primary solution through the needle valve 14. In many cases, the secondary solution will completely cover float 29 to perhaps a level indicated as level 39. Since the infusion rate is controlled by a flow control valve (not shown) on tubing 31, the secondary solution in the calibrated chamber 10 will be administered at the same continuous rate as was the primary solution, unless changed by the nurse.

Alternately, the secondary solution from container 37 can be used to dilute a drug which can be injected into calibrated chamber 10 through rubber sealed injection port 21. In this way, the secondary solution in container 37 can be used as a diluent for several different drugs which may not be compatible with the primary solution.

Since in many cases, it is desirable that minimum secondary solution be mixed with the primary solution, it may be readily seen that if a small amount of primary solution in calibrated chamber 10 is sufficient to raise float 29 to shut off the flow of primary solution, there will never be a large amount of primary solution interiorly to calibrated chamber 10 and interfluid mixing is reduced to a minimum. There will, of course, be also a small amount of mixing in the drip chamber 26.

If however, it is desired, to mix the secondary solution, a measured amount or an injected amount, with the primary solution, this may be easily achieved by means of flow valve 13. Flow valve 13 bypasses the float valve and permits direct filling of calibrated chamber 10 by primary solution. As indicated, the sides of chamber 10 are calibrated and by means of regulating flow valve 13 the amount of primary solution is regulated. To this regulated amount of primary solution, the secondary solution, either through flow valve 19 or by injection through rubber sealed injection port 21, is entered into calibrated chamber 10. If a third solution is desired to be entered into the calibrated chamber, this is easily accomplished by injection through port 21.

In addition, the invention is not to be limited to means of addition of a secondary solution by the method shown, as for example, a plurality of solutions in their separate containers may be transmitted into the calibrated chamber 10 in the manner accomplished for the secondary solution.

All of the solutions interiorly to the calibrated volumetric chamber 10 will pass around float 29 and into drip tube 27 of drip chamber 26 and into tubing 31. When the solutions have dropped to a level that float 29 permits fluted shaft 15 to drop, more primary solution will begin to enter the chamber.

It is noted that the primary solution comes back on line immediately after the level of the secondary solution in the calibrated chamber drops to a point below which needle valve 14 is permitted to open. Thus there is continuous fluid flow with no interruptions after the secondary solution has passed. It is anticipated, because of the distances float 29 must rise and fall to pass primary solution, that the float valve will be operating at all times when only primary solution is being passed.

Figure 2:
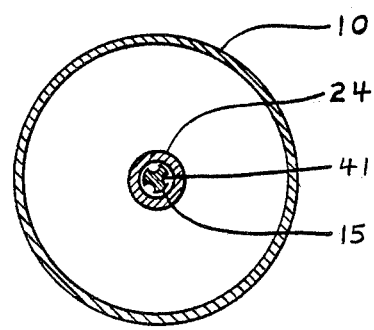
FIG. 2 is a cross-sectional view of the automatic sequential fluid flow apparatus of FIG. 1 taken along sectional lines II—II.

Referring now to FIG. 2, a cross-sectional view taken along sectional line II—II of FIG. 1 is detailed.

Proceeding from the outside inward, calibrated chamber 10 is shown surrounding on all sides the valve guide 24 of needle valve assembly 14. Central to valve guide 24 is fluted shaft 15 showing, in FIG. 2, three flutes 41. It is noted, in referring to FIG. 1, that the flutes are cut to a depth longitudinally in fluted shaft 15 that they do not ride up far enough on pointed end 16 so that a completed seal is not achieved at the juncture of the two differently sized passageways. Since it is desirable that there be minimum clearance between the exterior walls of fluted shaft 15 and the interior walls of valve guide 24, the flutes are necessary to allow the passage of the primary solution down fluted shaft 15. It is realized of course that a smaller shaft 15 could be substituted for fluted shaft 15 without impairing the invention, yet the more play or clearance there is between the shaft and the valve guide, the more opportunity there is for incomplete seal of the needle valve, or of hangup, situations which are not desirable.

It is readily noticed that one of the obvious advantages of the subject invention is that a nurse may infuse the secondary solution, nominally a drug, in a measured amount, without having to watch when the measured amount has passed and restart the primary solution. Additionally, if the same drug or secondary solution is given a patient in measured amounts at various intervals of time, sufficient solution may be placed in container 37 which, if calibrated, will permit the required amounts to be given over a period of time by periodic opening of flow valve 19, without the need for a new container for each new application of the drug.

While a preferred embodiment of the invention has been shown and described, it would be understood that there is no intent to limit the invention by such disclosure, but rather it is intended to cover all modifications and alternate constructions falling within the spirit and the scope of the invention as defined in the appended Claims.

I claim:

1. In combination with an intravenous administration set having interconnected primary solution container, calibrated volumetric chamber, and drip chamber for infusion of primary solution into a patient's body, an improvement for controlling non-mixing sequential fluid flow comprising float valve means positioned within the calibrated volumetric chamber operably controlling the primary solution entering the calibrated volumetric chamber, said float valve means defining a float element and a needle valve assembly operatively connected thereto, said needle valve assembly being connected in fluid communication with said primary solution container and being situated upstream from said float element so as to be operated by the buoyant movement of the float element, and said float element constructed to conform to the bottom and sides of the calibrated chamber, said float element so arranged with said needle valve assembly to float in close proximity to said calibrated volumetric chamber bottom; and means introducing a secondary solution into the said chamber, said means including a secondary solution container, tubing interconnecting said secondary solution container and the calibrated chamber, and a flow valve disposed in said tubing, said float valve means operably controlled by the secondary solution in the calibrated chamber whereby the flow of the secondary solution into the calibrated chamber may be controlled by the secondary solution flow valve in order that minimum secondary solution present in the calibrated chamber operates said float, and said float valve means controls the entry of primary solution into the calibrated chamber through said needle valve assembly following termination of secondary solution with minimum mixing of solutions.

2. The improvement in automatic sequential fluid flow apparatus as defined in claim 1 wherein said needle valve assembly comprises an elongated cylinder, the passageway through said cylinder being a first smaller diameter passageway stepped into a second larger diameter passageway, the first passageway operably connected to the primary solution container; and elongated shaft means, the second passageway adapted to receive said elongated shaft means, said shaft means being of diameter larger than said first passageway diameter whereby when said float element rises in the calibrated chamber, said shaft means is urged against the orifice formed at the step between the first and second passageways and the flow of the primary solution is controlled.

3. The improvement in automatic sequential fluid flow apparatus as defined in claim 2 wherein said shaft means first end defines a pointed end to engage the orifice formed at the step between the first and second passageway.

4. The improvement in automatic sequential fluid flow apparatus as defined in claim 3 wherein said shaft means comprises flutes extending lengthwise whereby the primary solution passing the end of the shaft may travel down the flutes to the float element and into the bottom of the calibrated volumetric chamber.

5. The improvements in automatic sequential fluid flow apparatus as defined in claim 4 further comprising means introducing the primary solution into the calibrated volumetric chamber interior, said means including flow valve means whereby primary solution may be introduced into the calibrated chamber separate from the primary solution controlled by said float valve means.

* * * * *